(12) United States Patent
Li et al.

(10) Patent No.: US 10,617,364 B2
(45) Date of Patent: Apr. 14, 2020

(54) SYSTEM AND METHOD FOR SNORING DETECTION USING LOW POWER MOTION SENSOR

(71) Applicant: Samsung Electronics Co., Ltd., Suwon-si (KR)

(72) Inventors: Yelei Li, Santa Clara, CA (US); Matthew C. Wiggins, San Jose, CA (US); Anabel M. De Proft, Mountain View, CA (US)

(73) Assignee: Samsung Electronics Co., Ltd. (KR)

( * ) Notice: Subject to any disclaimer, the term of this patent is extended or adjusted under 35 U.S.C. 154(b) by 528 days.

(21) Appl. No.: 15/370,468

(22) Filed: Dec. 6, 2016

(65) Prior Publication Data

US 2018/0116606 A1    May 3, 2018

Related U.S. Application Data

(60) Provisional application No. 62/413,494, filed on Oct. 27, 2016.

(51) Int. Cl.
*A61B 5/00* (2006.01)
*A61B 5/113* (2006.01)

(52) U.S. Cl.
CPC .......... *A61B 5/7278* (2013.01); *A61B 5/113* (2013.01); *A61B 5/4806* (2013.01); *A61B 5/681* (2013.01); *A61B 5/7225* (2013.01); *A61B 5/742* (2013.01); *A61B 5/7405* (2013.01); *A61B 5/7455* (2013.01); *A61B 2562/0219* (2013.01)

(58) Field of Classification Search
CPC ......... A61B 5/11; A61B 5/113; A61B 5/1123; A61B 5/4806; A61B 5/7278
See application file for complete search history.

(56) References Cited

U.S. PATENT DOCUMENTS

| | | | | |
|---|---|---|---|---|
| 3,729,587 A * | 4/1973 | McGill, Jr. | ......... | H04L 27/1563 375/334 |
| 4,207,543 A * | 6/1980 | Izakson | .................... | H03G 5/16 327/553 |
| 5,774,837 A * | 6/1998 | Yeldener | ................. | G10L 19/12 704/206 |
| 8,771,205 B2 * | 7/2014 | Gavriely | ................ | A61B 5/053 600/532 |
| 9,060,880 B2 * | 6/2015 | Van Beest | ............ | A61B 5/4561 |
| 9,675,800 B2 * | 6/2017 | Li | ........................ | A61N 1/3601 |

(Continued)

FOREIGN PATENT DOCUMENTS

WO    2015/175673 A1    11/2015

OTHER PUBLICATIONS

Hao, Tian, Guoliang Xing, and Gang Zhou. "iSleep: unobtrusive sleep quality monitoring using smartphones." Proceedings of the 11th ACM Conference on Embedded Networked Sensor Systems. ACM, 2013. Found via ACM Digital Library and freely available via Google Scholar (url: http://www.cse.buffalo.edu/~lusu/cse721/papers/iSleep%20Unobtrusive%20Sleep%20Quality%20Monitoring%20using%20Smartphones.pdf).

*Primary Examiner* — Max F Hindenburg
(74) *Attorney, Agent, or Firm* — McAndrews, Held & Malloy, Ltd.

(57) ABSTRACT

Provided is an electronic device to monitor a user's biological measurements, where a sensor is configured to acquire a raw signal from a user, and the electronic device determines a snoring signal from the raw signal by appropriately processing the raw signal.

20 Claims, 7 Drawing Sheets

(56) References Cited

U.S. PATENT DOCUMENTS

| | | | |
|---|---|---|---|
| 9,849,289 B2* | 12/2017 | Mashiach | A61N 1/0526 |
| 10,052,048 B2* | 8/2018 | Klewer | A61B 5/0816 |
| 10,098,583 B2* | 10/2018 | Shigeto | A61B 5/1135 |
| 10,159,429 B2* | 12/2018 | Heinrich | A61B 5/1128 |
| 2005/0065560 A1 | 3/2005 | Lee et al. | |
| 2007/0100666 A1 | 5/2007 | Stivoric et al. | |
| 2008/0069469 A1* | 3/2008 | Yan | H04N 19/117 |
| | | | 382/261 |
| 2010/0030085 A1 | 2/2010 | Rojas Ojeda et al. | |
| 2012/0272958 A1 | 11/2012 | Krzi et al. | |
| 2014/0107493 A1 | 4/2014 | Yuen et al. | |
| 2014/0180153 A1* | 6/2014 | Zia | A61B 7/00 |
| | | | 600/528 |
| 2016/0151603 A1 | 6/2016 | Shouldice et al. | |
| 2018/0000426 A1* | 1/2018 | Li | A61B 5/0022 |

\* cited by examiner

SYSTEM AND METHOD FOR SNORING DETECTION USING LOW POWER MOTION SENSOR

RELATED APPLICATIONS

This application claims the benefit of the U.S. Provisional Application 62/413,494, filed on Oct. 27 2016, the disclosure of which is incorporated herein in its entirety by reference. The U.S. application Ser. No. 14/928,072 is incorporated in its entirety by reference.

BACKGROUND OF THE INVENTION

The present disclosure relates to measuring a user's body signals, and more particularly, to a system and method for snoring detection using a low power motion sensor.

Snoring is a common sleep issue among all ages and both genders. It is thought that approximately 45 percent of the population snores and 25 percent are habitual snorers. Hypertension and coronary heart disease are statistically more common in individuals with habitual snoring. Multivariate analyses shows that males are more prone to be habitual snorers, with significant risk factors being 40 years old or older, obesity, smoking, and the use of alcohol.

BRIEF SUMMARY OF THE INVENTION

Provided are a system and method for snoring detection using a low power motion sensor. An example of an embodiment may include a method for detecting a raw signal from a user via a motion sensor, determining a snoring signal from the raw signal based on an adaptive frequency threshold, and providing feedback to the user based on the snoring signal.

Another example of an embodiment may include a non-transitory machine-readable medium storing machine executable instructions that when executed causes a computing system to control operations that detects a raw signal from a user via a motion sensor, determines a snoring signal from the raw signal based on an adaptive frequency threshold, and provides feedback to the user based on the snoring signal.

Still another example of an embodiment may include an electronic device comprising at least one motion sensor configured to detect a raw signal from a user, a processor configured to determine a snoring signal from the raw signal based on an adaptive frequency threshold, and an output device configured to provide feedback to the user based on the snoring signal.

Additional aspects will be set forth in the description that follows and/or learned by practice of the presented example embodiments.

BRIEF DESCRIPTION OF SEVERAL VIEWS OF THE DRAWINGS

These and/or other aspects will become apparent and more readily appreciated from the following description of the examples of the various embodiments, taken in conjunction with the accompanying drawings.

DETAILED DESCRIPTION OF THE INVENTION

Figure 1:
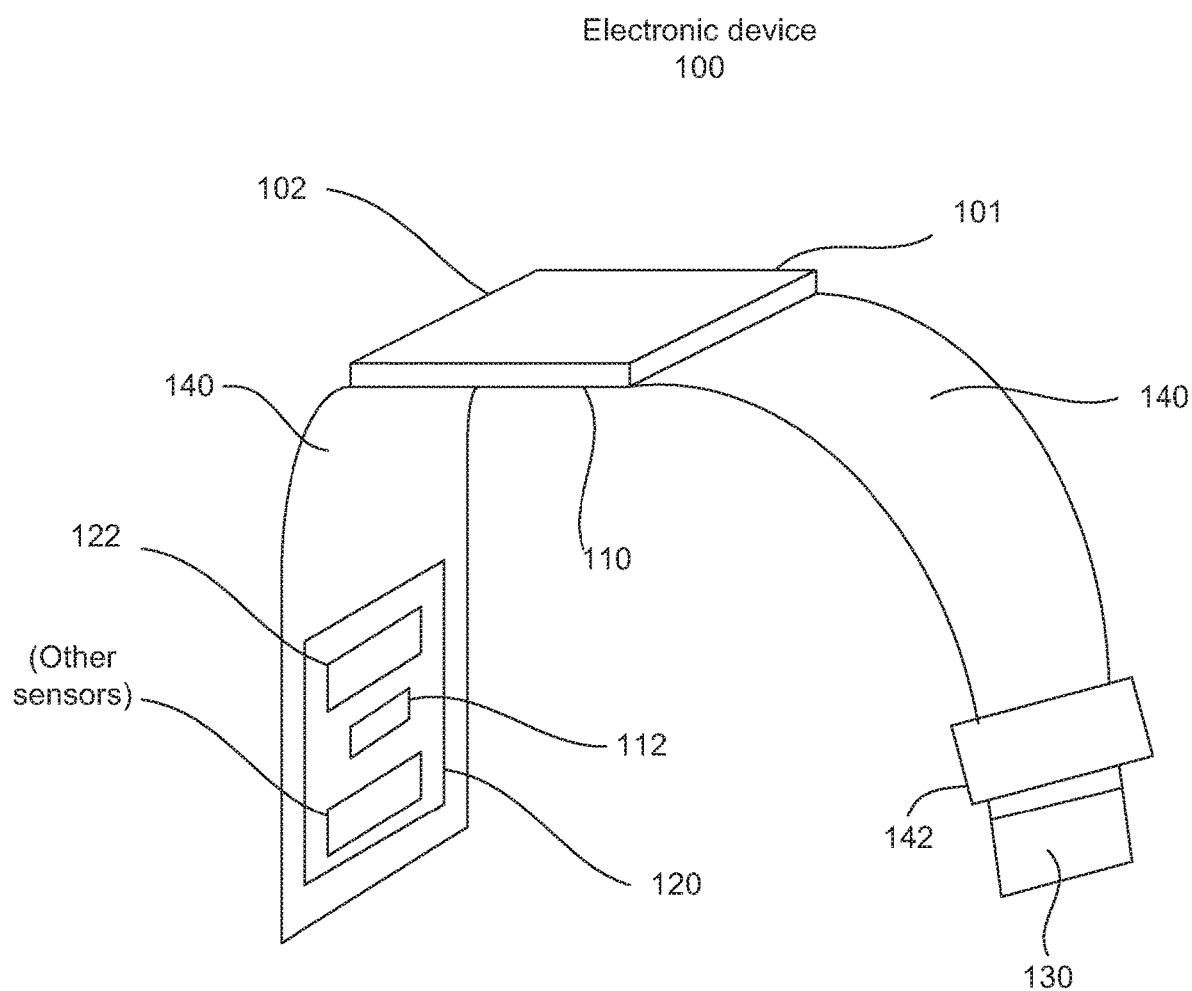
FIG. 1 is a diagram illustrating an example of an electronic device in accordance with an embodiment of the present disclosure.

Advantages and features of one or more embodiments of the present disclosure may be understood more readily by reference to the following detailed description of the embodiments and the accompanying drawings.

In this regard, the described embodiments should not be construed as being limited to the descriptions set forth herein. Rather, these embodiments are provided as examples so that this disclosure will be thorough and complete and will fully convey the concept of the disclosure to one of ordinary skill in the art. The appended claims illustrate some of the embodiments of the present disclosure.

Like reference numerals refer to like elements throughout the specification. All terms including descriptive or technical terms used herein should be construed as having meanings that are obvious to one of ordinary skill in the art. When a term has an ambiguous meaning due to evolving language, precedent cases, or the appearance of new technologies, the meaning of a term used in this disclosure should first be clarified by its usage and/or definition in this disclosure. If further clarification is needed, the term should then be clarified as one of ordinary skill in the art would have understood the term in context of the disclosure at the time of the disclosure.

When a part "includes" or "comprises" an element, unless there is a particular description contrary thereto, the part can further include other elements. The term "unit" in the embodiments of the present disclosure means a software component or a hardware component that performs a specific function. The hardware component may include, for example, a field-programmable gate array (FPGA) or an application-specific integrated circuit (ASIC).

Software component may refer to executable code and/or data used by the executable code in an addressable storage medium. Thus, software components may be, for example, object-oriented software components, class components, and task components, and may include processes, functions, attributes, procedures, subroutines, segments of program code, drivers, firmware, micro codes, circuits, data, a database, data structures, tables, arrays, or variables.

A function provided by a "unit" may be divided into additional components and "units."

Reference will now be made in detail to embodiments, examples of which are illustrated in the accompanying drawings. In this regard, the present embodiments may have different forms and should not be construed as being limited to the descriptions set forth herein.

In the following descriptions, well-known functions or constructions are not described in detail so as not to obscure the embodiments with unnecessary detail.

A long term effect of snoring may be unrestful sleep that may cause excessive sleepiness during daytime and increases the risk of cardiovascular disease. By detecting and monitoring snoring symptoms of an individual, valuable information can be extracted for chronic diseases treatment such as hypertension, sleep apnea, etc., and aid in health management such as weight management, stress level monitoring, etc.

Snoring may be alleviated by some lifestyle modifications such as, for example, elevating the head of a bed approximately 6 to 8 inches, losing weight, avoiding alcohol before going to sleep, not eating a full meal just before bed time, stop smoking, changing sleep position, etc. However, as a person sleeps, it may be beneficial to have a device that alerts the user to snoring so that the user can adjust the sleep position to help reduce snoring.

The present disclosure describes a framework for detecting a snoring event using a low power motion sensor. The present disclosure includes a low power motion sensor that detects and extracts a snoring event from a low power motion sensor placed at one of various body positions or remote locations. The present framework is potentially beneficial for sleep apnea monitoring, hypertension management, cardiovascular disease management, and lifestyle management. Various embodiments may monitor snoring symptoms using a low power motion sensor, so that the present system can provide feedback and motivation to a user to improve his/her lifestyle.

One embodiment of the disclosure may include a low power motion sensor (e.g., an accelerometer, a gyroscope) that acquires a raw signal. The sensor may monitor and detect the raw signal using one or more channels of these sensors. The sensor measurement locations can be flexible: possible locations include attachment to the body (e.g., neck, chest, and wrist) or other locations where the sensor is not attached to the body (e.g., bedside, underneath mattress). Various embodiments may include a high-sensitivity motion sensor combined with the present framework to extract a subtle snoring signal from a raw signal. In some embodiments, a device placed in certain beside position may provide respiratory and snoring information for detection. Various embodiments may also use a microphone where the sounds detected may be used to help determine the snoring signals. When placed beneath a mattress, for example, underneath the subject whose signals are being detected, respiratory signal may be detected by the motion sensor for processing to determine the snoring signal.

FIG. 1 is a diagram illustrating an example of an electronic device in accordance with an embodiment of the present disclosure. Referring to FIG. 1, an electronic device 100, a version of which may be wearable on a wrist as shown in FIG. 1, has a microphone 101, a display 102, processors 110 and 112, a sensor module 120, a battery 130, a band 140, and a clasp 142. The sensor module 120 may include a sensor 122. The processor 110, or the CPU 200, or the processor 112 may also be referred to as a diagnostic processor, and may be able to execute instructions. Accordingly, a diagnostic processor may be, for example, a digital signal processor, a controller, a use specific processor, a general processor, and so on. At times, for ease of description, a diagnostic processor may also generally refer to a combination of various hardware (either described above or below).

Although an embodiment of the electronic device 100 is shown to be worn on a wrist, various embodiments of the disclosure need not be so limited. The electronic device 100 may also be designed to be worn on other parts of the body such as, for example, on an arm (around the forearm, the elbow, or the upper arm), on a leg, on the chest, on the head like a headband, on the throat like a "choker," and on an ear. The electronic device 100 may also be configured such that it is not meant to be worn, but may be placed nearby the user such as, for example, under the mattress, or near the user. The electronic device 100 may be able to communicate with other electronic devices the user owns or has access to such as, for example, a smart phone, or a laptop. The electronic device 100 may also be able to communicate with various medical devices at a hospital or a doctor's office. This will be described in more detail with respect to FIG. 3.

The microphone 101 may be used to detect audible sound such as breathing, snoring, and the like. Various embodiments of the electronic device 100 may also be able to communicate with an external microphone (not shown). The microphone 101 may be optional in some embodiments.

The display 102 may output information related to snoring and/or other biosignals or biometric data that may be monitored by the electronic device 100. In addition to snoring, the other signals monitored by the electronic device may be, for example, heart (pulse) rate, pulse morphology (shape), pulse spacing (inter-beat intervals), respiration (breathing) rate, and blood pressure. The display 102 may also output instructions to the user or others in the use of the electronic device 100 or use of other measurement devices, as well as status and diagnostic results, for example. Additionally, the display 102 may be used to output alerts, for example, to notify of the user snoring. Accordingly, the display 102 may emit a steady light or a blinking light. The display 102 may also comprise a discrete light such as, for example, an LED that may be used to shine to indicate the user is snoring. The light may be used, for example, to visually alert those monitoring the user, and also to possibly train a user who is sensitive to ambient light while sleeping. Other alerts may be by sound or vibrations, for example.

The processor 110 can receive the monitored signals via a sensor in the sensor module 120. The sensor module 120 may include, for example, the sensor 122 that may acquire signals from the user's wrist when the electronic device 100 is worn on the wrist, as well as provide other information that may indicate the user's body position, motion, and the like. The sensor 122 may be, for example, an accelerometer, a gyrometer, and the like. The processor 112 may control the sensor 122, and may also process the signals monitored by the sensor 122. Various embodiments of the disclosure may have the processor 110 also perform the functions of the processor 112. Various embodiments of the disclosure may also have two or more sensors for detecting various biosignals.

If there is more than one sensor, the other sensor(s) may be similar to the sensor 122 or a different type of sensor such as, for example, a thermometer for taking the user's temperature. Various embodiments may include different numbers of sensor modules. For example, some embodiments may only have one sensor module, while other embodiments may have 2 or more sensor modules.

The battery 130 is configured to provide power for the electronic device 100. The battery 130 may be charged using a wired charging system or a wireless charging system. The band 140 may be wrapped around a wrist and the electronic device 100 may be held on the wrist by using the clasp 142.

Figure 2:
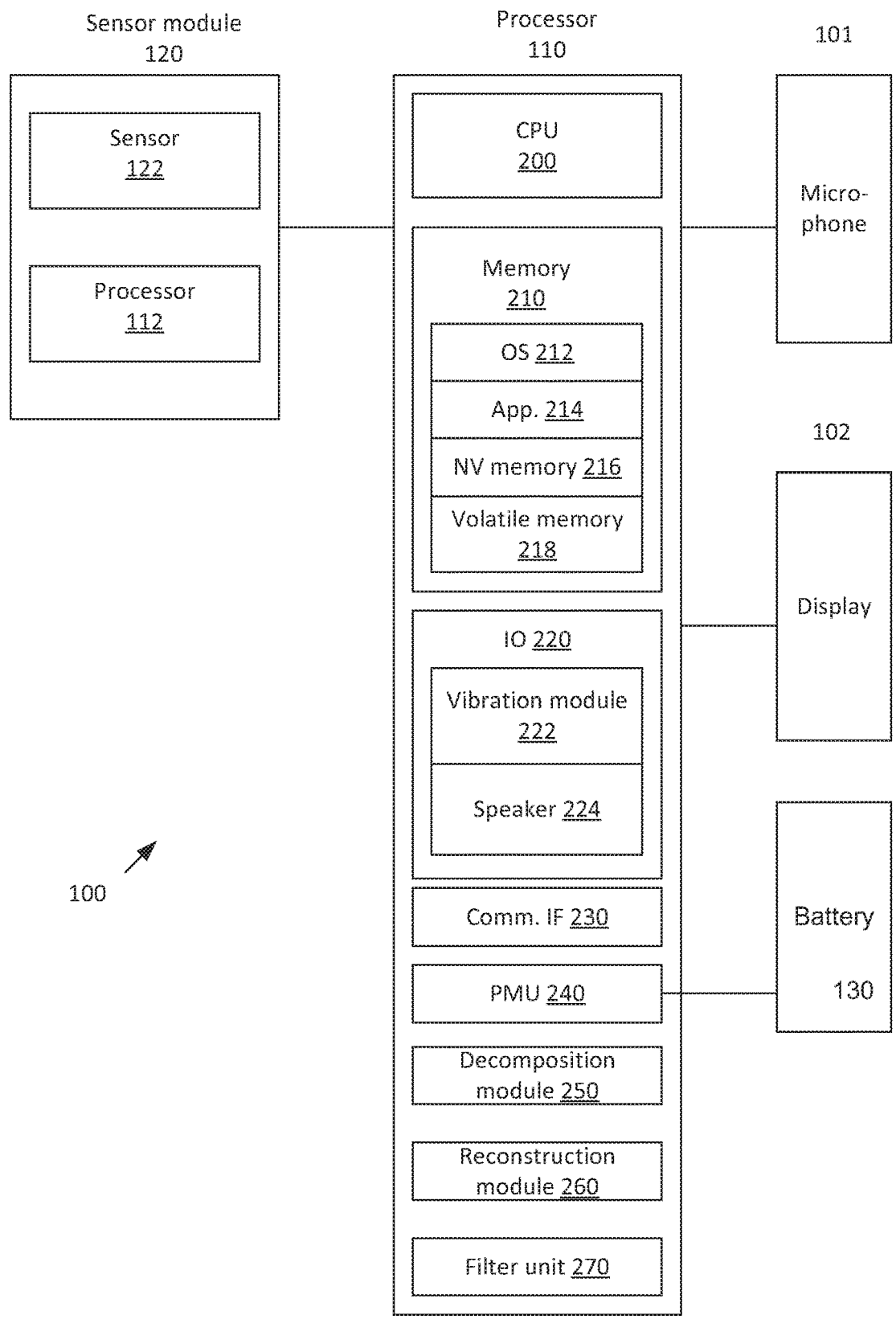
FIG. 2 is a high-level block diagram of an example of an electronic device in accordance with an embodiment of the present disclosure.

FIG. 2 is a high-level block diagram of an example of an electronic device in accordance with an embodiment of the present disclosure. Referring to FIG. 2, there is shown the electronic device 100 with the microphone 101, the display 102, the processor 110, the sensor module 120, and the battery 130. The microphone 101 may be used to detect audible sounds. Output to the display 102 can be controlled, for example, by the processor 110. The display 102 may also include input devices (not shown) such as, for example, buttons, dials, and touch sensitive screen.

The processor 110 may include a CPU 200, memory 210, an input/output (IO) interface 220, a communication interface 230, a power management unit (PMU) 240, a decomposition module 250, a reconstruction module 260, and a filter unit 270.

While the processor 110 is described as including these various devices, other embodiments may use other architectures where the different functionalities are grouped differently. For example, the grouping may be in different integrated circuit chips. Or the grouping may be combining different devices such as the IO interface 220 and the communication interface 230 together, or the decomposition module 250 and the reconstruction module 260 together.

The CPU 200 may control operation of the sensor module 120 as well as receive monitored signals from the sensor module 120. The CPU 200 may control the electronic device 100, including processing the monitored signals from the sensor module 120, displaying the processed signals on the display 102, receiving input from the display 102, interfacing with various devices via the IO interface 220 or the communication interface 230 by executing instructions in the memory 210. The IO interface 220 may be used by the CPU 200 to interface with the display 102.

The processor 112 may operate using different architectures in different embodiments. For example, the processor 112 may use the memory 210 to store instructions to execute, or the processor 112 may have its own memory (not shown) for its instructions. Although some embodiments have separate processors 110 and 112, the various embodiments need not be limited so. There may be one processor 110 that controls the functionality of the electronic device 100, or there may be multiple processors for the electronic device 100.

The memory 210 may include non-volatile memory 216 and volatile memory 218. The operating system and applications may be stored in the non-volatile memory 216. Various embodiments of the disclosure may use different memory architectures that are design and or implementation dependent.

The communication interface 230 may allow the electronic device 100 to communicate with other devices via, for example, a wired or wireless protocol such as USB, Bluetooth, Near Field Communication (NFC), and WiFi. The communication interface 230 may allow reception of sounds detected by an external microphone (not shown). Accordingly, the sound detected by the external microphone may be used in place of, or in concert with, the sound picked up by the microphone 101. The PMU 240 may control receiving power from an outside source (not shown), charging the battery 130, as well as allocation of power to the different parts of the electronic device 100.

In some embodiments, the electronic device 100 may comprise a decomposition module 250 that may function to decompose, for example, an input signal to multiple frequency bands using time-frequency transforms. The reconstruction module 260 may operate to reconstruct, for example, the decomposed signals from the decomposition module 250 to refine and access desired components of the original signal. Decomposition and reconstruction of a signal is explained in more detail in the U.S. application Ser. No. 14/928,072, which is incorporated in its entirety by reference. The filter unit 270 may be used to select specific frequencies from a signal. Accordingly, the filter unit 270 may be one or more of low-pass filter, band-pass filter, and high-pass filter. The functionality of the filter unit 270 may be implemented in hardware and/or software.

Figure 3:
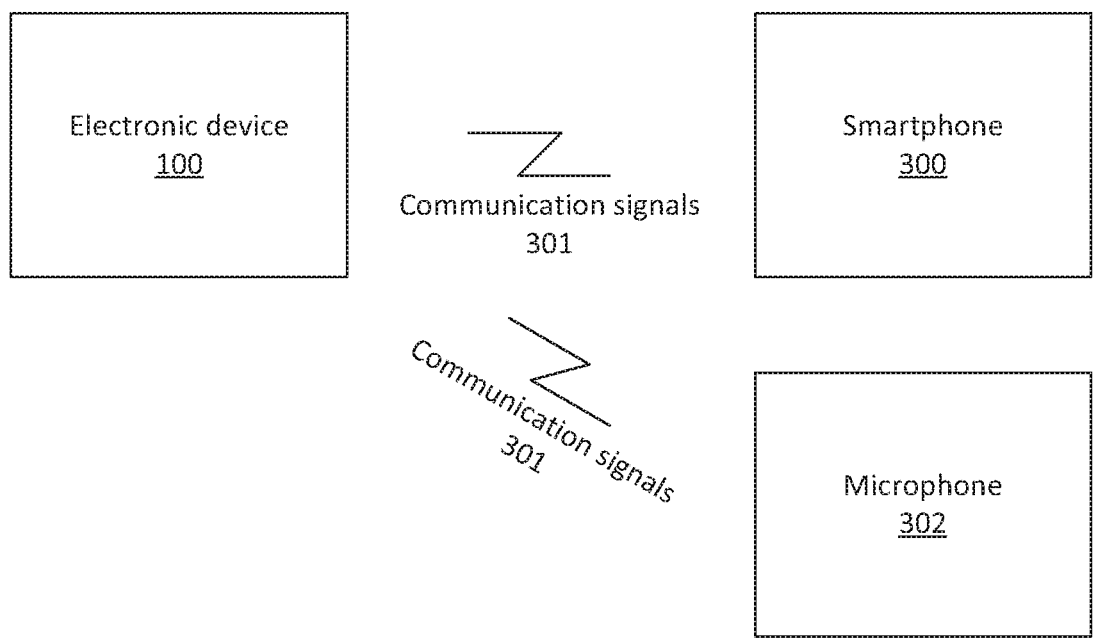
FIG. 3 is an illustration of an example of an electronic device in a communication network in accordance with an embodiment of the present disclosure.

FIG. 3 is an illustration of an example of an electronic device in a communication network in accordance with an embodiment of the present disclosure. Referring to FIG. 3, there is shown the electronic device 100, a smartphone 300, and a microphone 302. The electronic device 100 may communicate with the smartphone 300 and/or the microphone 302 using the communication interface 230. The communication may be via the communication signals 301, where the communication may be directly between the electronic device 100 and a smartphone 300, directly between the electronic device 100 and the microphone 302, or include other elements between the electronic device 100 and the smartphone 300 and/or the microphone 302.

One of the applications 214 of the electronic device 100 may allow the smartphone 300 to control at least some operation of the electronic device 100. For example, the electronic device 100 may output to the display 102 a result of the processing by the processor 110, and/or the same result may be transmitted to, for example, the smartphone 300. The user may also select an option either on the electronic device 100 or on the smartphone 300. The options may be, for example, to start a biosignal monitoring process by the electronic device 100 or to stop the biosignal monitoring process.

Since the smartphone 300 has a larger display, it can be easier for the user to view a result or to select an option on the smartphone 300 rather than on the electronic device 100. Accordingly, the smartphone 300 (or other devices to which the electronic device 100 is connected) may display more information than can be seen on the display 102 at one time. It should be noted that the smartphone 300 may not generally be necessary for operation of the electronic device 100.

Additionally, the electronic device 100 may communicate with the microphone 302 to receive sounds detected by the microphone 302. While the microphone may be used for various purposes, one purpose may be to detect sounds made by a user when the user is sleeping. Accordingly, the microphone 302 may detect breathing and/or snoring sound made by the user, and this sound can be transmitted to the electronic device 100. The electronic device 100 may then be able to process and correlate the sound signals to the raw signals detected by, for example, the sensor(s) 122.

Figure 4:
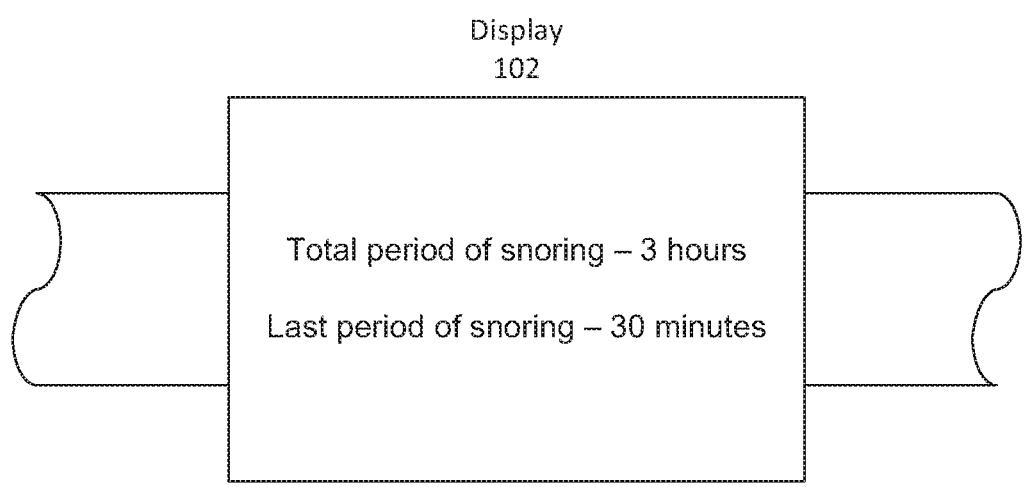
FIG. 4 is an example of a notification by the electronic device to the user in accordance with an embodiment of the present disclosure.

FIG. 4 is an example of a notification by the electronic device to the user in accordance with an embodiment of the present disclosure. Referring to FIG. 4, status may be shown on the display 102 when no user intervention is required. The status may indicate, for example, a biosignal monitoring status by the electronic device 100. The status may summarize, for example, periods of times for snoring that the electronic device 100 has detected. The status may also comprise other biosignal data such as, for example, a correlation between the periods of snoring, intensity of snoring, and periods of sleep apnea where the user does not breathe. The intensity of snoring may be measured, for example, in decibels via the microphone 101 in the electronic device 100 or an external microphone 302. The intensity of snoring may also be measured, for example, by biosignals such as vibrations of the body detected by the sensor 122 during times of snoring.

While various biosignal statuses may be displayed, descriptions here will be focused for the most part on snoring related events. When the processor 110, which may be referred to as a diagnostic processor, determines that the monitored signals from the sensor 122 indicates that further measurements need to be taken, instructions to the user may be displayed on the display 102. The instructions may indicate, for example, that the user needs to adjust the electronic device 100 to be tighter on the wrist so that the sensor 122 may acquire more accurate reading. An output indication of snoring may be provided via, for example, the display 102, vibration via the vibration module 222, and/or an audio alert via the speaker 224. The output via the visual display 102 may also include, for example, a visual alert such as a flashing light. Some of these outputs may be used, for example, as feedback for the user to adjust the body position to reduce snoring. The feedback may be set, for example, for specific snoring intensity.

The electronic device 100 may also display via the visual display 102 and/or the speaker 224 instructions for setting up a connection between the microphone 302 and the electronic device 100. The sounds detected by the microphone 302 may be used to supplement the raw signals detected by the electronic device 100. Some embodiments may consider the raw signals to include the sounds from the microphone 302 and/or the microphone 101.

Various embodiments of the disclosure may include different instructions for different types of biosignals being monitored, including instructing the user to consult a medical professional. Accordingly, the electronic device 100 may have different levels of instructions and monitoring depending on the needs of the user and/or the medical professional.

Figure 5A:
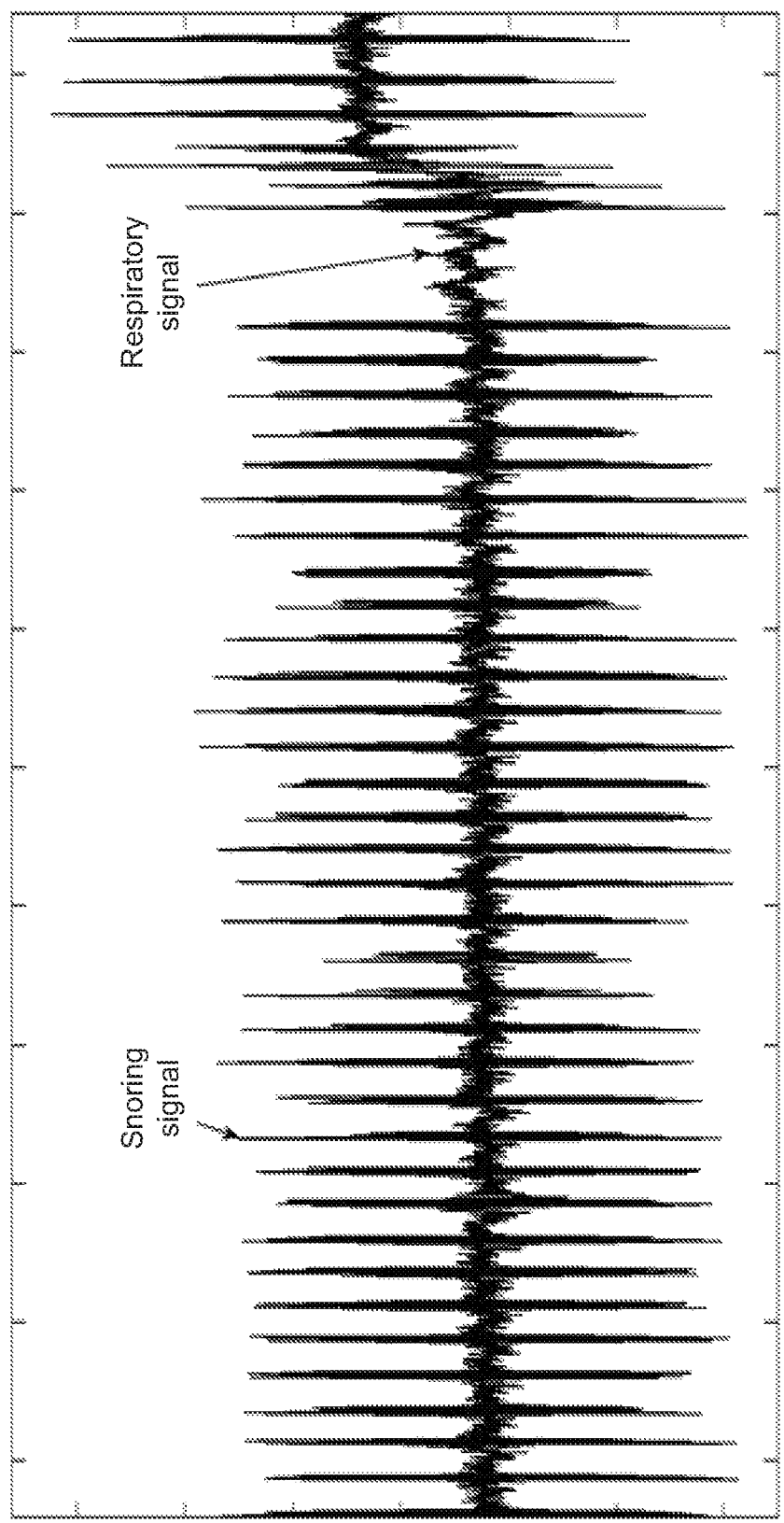
FIG. 5A is an example of a raw signal from one axis of an accelerometer in accordance with an embodiment of the present disclosure.

FIG. 5A is an example of a raw signal from one axis of an accelerometer in accordance with an embodiment of the present disclosure. Referring to FIG. 5A, there is shown a raw signal that may comprise various biosignals of a user. There is a large snoring signal that may be overlaid with other signals such as, for example, a respiratory signal. This can be seen on the right hand side of the graph where during certain periods when the snoring signals are absent, the respiratory signal can be seen more clearly.

The raw signal may be acquired by the sensor 122 that may be, for example, a low power motion sensor (e.g., an accelerometer, a gyroscope). The sensor 122 may detect the raw signal from one or more of its available channels. The sensor measurement locations may be flexible with possible locations including attachment to the body (e.g., neck, chest, and wrist) or more remote locations (e.g., bedside, underneath mattress). Various embodiments may include a high-sensitivity motion sensor combined with the present framework to extract even a subtle snoring signal from a raw signal.

Figure 5B:
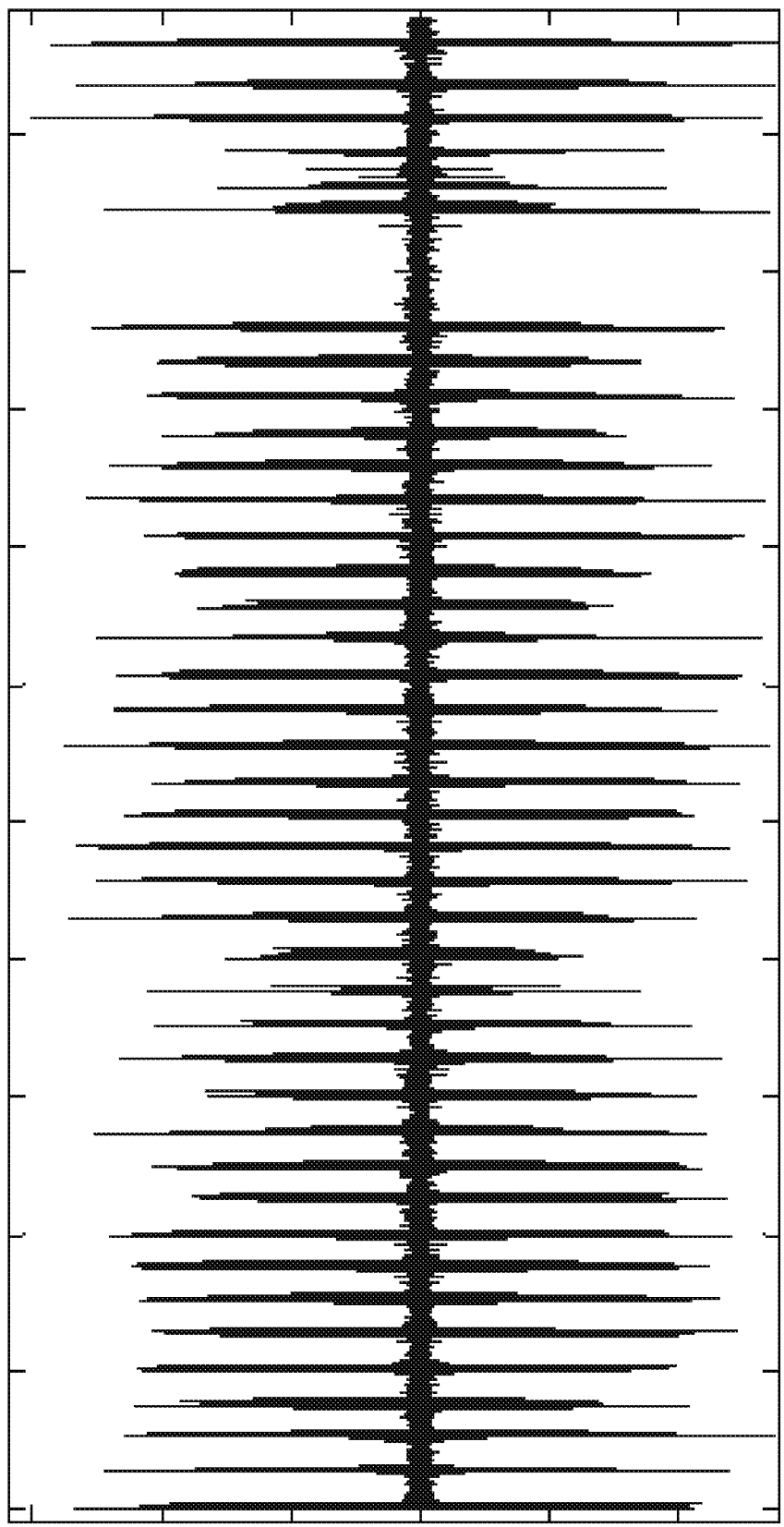
FIG. 5B is an example of a filtered signal in accordance with an embodiment of the present disclosure.

FIG. 5B is an example of a filtered signal in accordance with an embodiment of the present disclosure. Referring to FIG. 5B, there is shown a filtered signal that has much of the respiration signal removed as well as removing modulation signals that may have been present. For example, the modulation signal at the right hand side of FIG. 5A that raised the amplitude of the snoring signal has been removed in FIG. 5B. Various embodiments may obtain a filtered snoring signal by using Wavelet decomposition to pre-process the raw signal and extract a desired frequency band, such as extracting a frequency that is greater than a desired threshold frequency (since a snoring signal frequency is generally greater than 6 Hz) for snoring detection. This may be performed, for example, using the decomposition module 250 and the reconstruction module 260.

While the raw signal may be pre-processed using various methods such as, for example, a time-frequency technique, various embodiments of the disclosure need not be limited to using time-frequency technique. In one embodiment, a finite impulse response (FIR) high-pass filter may filter out respiration and heart beat information. In another embodiment, time-domain derivative operation may be used to filter out low frequency pattern.

Figure 6:
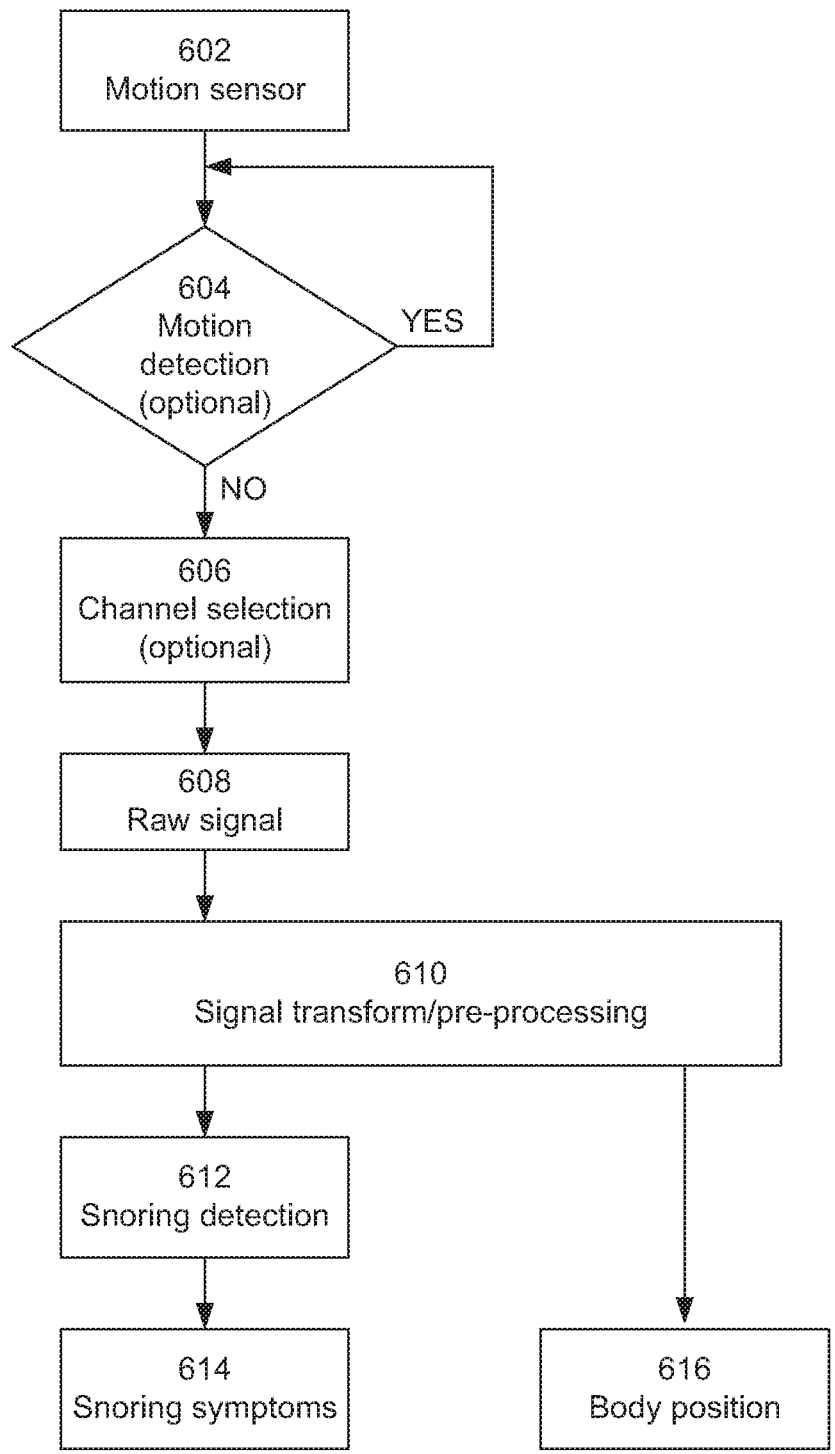
FIG. 6 is an example flow chart for processing an input signal in accordance with an embodiment of the present disclosure.

FIG. 6 is an example flow chart for processing an input signal in accordance with an embodiment of the present disclosure. Referring to FIG. 6, at 602, a motion sensor such as, for example, the sensor 122 may detect signals from the user's body. The detected signal may be a raw signal such as that shown in FIG. 5A.

Motion detection at 604 may be optional since snoring mostly occurs when a user is sleeping, and so the user may be assumed to be stationary. However, if motion detection is available at 604, and if motion is detected to be above a threshold level, then the snoring detection algorithm may wait until the user motion is below the threshold if the user is moving about fitfully during sleep. A sensor such as an accelerometer on the sensor module 120 may monitor/detect user motion. Motion detection may be taken into account if, for example, other biosignals are to be detected. While some biosignals may not be affected by user motion, other monitored biosignals provide better signals when the user is substantially stationary.

Channel selection at 606 may not be needed if there is only one channel for the sensor 122. For cases where there is more than one channel, various embodiments may select a channel with the strongest signal, or the next channel that is available that is above a threshold level. The channel selected may depend on, for example, the clarity of signals, power needed to monitor the biosignal for snoring, as well as other biosignals desired to be monitored, among other criteria. Different criteria may be determined for different embodiments. For example, if measurement sensors such as an accelerometer and a gyrometer are present, the channel candidates may include outputs for each of the three axes of the accelerometer, a magnitude of the accelerometer, and multiple outputs for the gyrometer for a multitude of channels from which to pick a channel. However, various embodiments of the disclosure need not be so limited.

According to one embodiment, an embodiment may further combine channels as signal fusion for signal quality enhancement purposes to form a new channel, further increasing the number of channels. Accordingly, an embodiment may select a channel based on, for example, one or more of recurrence rate analysis, determinism of dominate (or dominant) frequency in frequency spectrum, entropy analysis, etc.

At 608, the raw signal from the selected channel of the sensor 122 is provided by the sensor 122. At 610 the raw signal is received for pre-processing by, for example, the processor 110 and/or 112. The raw signal (from 608) may be from the selected channel or directly from the measurement sensor, depending on whether there is a channel selection process at 606. The raw signal may be pre-processed to remove respiration artifacts and high frequency disturbances by using techniques such as, for example, time-frequency processing technique, and/or a time-domain processing technique. Time-frequency processing technique includes, among others, wavelet coefficient reconstruction, and time-domain processing technique includes, among others, band-pass filtering, low-pass filtering, and high-pass filtering. An embodiment may use a finite impulse response (FIR) high-pass filter to filter out respiration and heart beat information. Accordingly, time-domain derivative operation may be used to filter out undesired frequencies.

An embodiment may pre-process the raw signal to obtain filtered snoring signal by using, for example, Wavelet decomposition. A desired frequency band may be greater than a desired threshold (since a snoring signal frequency is generally greater than 6 Hz) for snoring detection. The filtering may be via the filter unit 270, or performed via digital signal processing using one or more diagnostic processors such as, for example, the processor 112 or the CPU 200.

Pre-processing at 610 may not be performed if, for example, the raw signal is determined to be a relatively clean signal where the snoring signal can be readily determined.

At 612, the snoring detection block may be applied to identify snoring onset locations or a snoring segment. For example, an embodiment may apply an adaptive frequency threshold to detect a snoring event. The adaptive frequency threshold may be varied, for example, for an individual to better detect the snoring signals. The snoring signals may vary in frequency from one individual to another. In another example, an embodiment may use a hold-off parameter to prevent false detections within a single event. In another example, an embodiment may determine one or more parameters such as energy, entropy, and a periodicity rate to detect whether a snoring event occurs in a given time window (e.g., 20 seconds).

At 614, the snoring symptom block may provide information such as, for example, snoring rate, snoring intensity, and beat by beat snoring interval. However, an embodiment of the disclosure is not limited to any or all of these information. Moreover, by combining the information from the snoring symptom block (614) with information from the body position block (616) an embodiment may statistically monitor and quantify causality correlation between a body position and snoring. Accordingly, an embodiment may provide customized information for a user regarding how to improve a sleeping habit based on the quantified causality correlation between the body position and snoring.

A body position may be determined by, for example, indicating to the user to sleep in a recommended sleep position. The sleep position may be, for example, on the user's back or side. By keeping track of body movements (how much it has turned in one direction or another) using the sensor 122, the electronic device 100 may be able to estimate the body position. Other embodiments may use, for example, a camera to view the body of the user and then analyze the position of the body. The camera may be external to the electronic device 100 or part of the electronic device 100.

In addition to providing instructions/guidance on sleeping position to alleviate snoring, feedback may be provided via the vibration module 222 and/or the speaker 224 whereby the user may be awakened. The user may then be prompted to change the body position to the desired position. The feedback may train the user such that the user is able to adjust the body position upon receiving the feedback without having to wake up.

While an embodiment was described in the flowchart of FIG. 6, it should be understood that other embodiments may use different processes that may show a different flow, with added functions, and/or removed functions. For example, various embodiments may process sounds detected by the microphone 101 and/or the microphone 302, along with the raw signals detected by the sensor(s) 122 to better determine a snoring signal. Still other embodiments may use the sounds detected by the microphone 101 and/or the microphone 302 to determine a snoring signal.

Accordingly, one embodiment of the disclosure may include a low power motion sensor that provides snoring signal extraction and event detection. Various embodiments may be able to provide time and frequency information extracted from the snoring signal. Various embodiments may further combine snoring detection and body position detection to statistically quantify correlation between snoring detection and body position detection to be able to provide feedback to user.

By continuously monitoring and learning about indicators including the quantified correlation between snoring detection and body position detection, various embodiments may further build a personalized model for coaching. For example, an embodiment may awaken the user using a notification (e.g., an alarm, a vibration of the wearable device having the low power motion sensor worn by the user, etc.) when snoring is detected. In another embodiment, a coaching application may suggest a better sleeping position to the user based on the quantified correlation between snoring detection and body position detection. In another embodiment, the feedback may be provided so that the user may learn to adjust his/her body position to reduce snoring without being awakened. The user may then be able to sleep in appropriate position(s) to reduce snoring with minimal (or no) notification. The electronic device may still be used to monitor snoring and other biosignals.

According, various embodiments may be potentially beneficial for managing various user habits and issues such as sleep apnea monitoring, hypertension management, and cardiovascular disease management. Various embodiments may further combine snoring information with heart beat and respiratory information for diagnosis/monitoring.

Accordingly, various embodiments may provide snoring detection to benefit lifestyle monitoring such as weight management, motivation of quitting a bad habit such as smoking and drinking. For example, an embodiment can use an indication of an improvement in snoring behavior as a parameter of lifestyle improvement.

According to one embodiment, the sensor 122 may be placed at various sensor measurement locations, such as being attached to a body of the user (e.g., neck, chest, and wrist) and other remote locations (e.g., bedside, underneath the mattress). Various embodiments may analyze frequencies greater than a desired threshold (e.g., 6 Hz) from a raw signal detected by a high sensitivity motion sensor, and extract a snoring signal. An embodiment may further extract a respiratory signal, a heartbeat signal, and a snoring signal simultaneously using different frequency bands from the raw signal detected from a low power motion sensor. The various signals may be analyzed and/or correlated to determine the health of the user. The present health/state of the user may also be monitored with respect to a baseline that may have been taken previously and/or with a history of the user. In this way, various signals from a user, including snoring signal, may be correlated over time.

Various embodiments of the disclosure may be written as computer programs and may be implemented in general-use digital computers that execute the programs using a non-transitory computer-readable recording medium.

Non-transitory computer-readable recording medium may include, for example, magnetic storage media (e.g., ROM, floppy disks, and hard disks), and optical recording media (e.g., CD-ROMs, or DVDs).

While various embodiments of the disclosure have been described with reference to the figures, it will be understood by those of ordinary skill in the art that various changes in form and details may be made therein without departing from the spirit and scope of the disclosure as defined by the following claims. Accordingly, the above embodiments and all aspects thereof are examples only and are not limiting.

What is claimed:

1. A method comprising:
   detecting a raw signal from a user via a motion sensor;
   determining a snoring signal from the raw signal based on an adaptive frequency threshold; and
   providing feedback to the user based on the snoring signal,
   wherein:
      the feedback comprises visual instruction to the user regarding sleeping position provided prior to determining the snoring signal.

2. The method of claim 1, wherein the feedback is one of a vibration, an audio alert, and visual alert.

3. The method of claim 1, wherein a microphone is used to detect audible sound from the user to supplement the detecting of the raw signal.

4. The method of claim 1, wherein the raw signal is detected by one of an accelerometer and a gyrometer.

5. The method of claim 1, comprising pre-processing the raw signal with one of time-domain processing and time-frequency processing.

6. The method of claim 5, wherein the time-domain processing comprises one of band-pass filtering and high-pass filtering.

7. The method of claim 5, wherein the time-frequency processing comprises wavelets coefficient reconstruction.

8. The method of claim 1, comprising, if there are multiple channels for monitoring the raw signal, selecting one of the multiple channels for monitoring the raw signal.

9. The method of claim 1, comprising tracking a body position of the user.

10. A non-transitory machine-readable medium storing machine executable instructions that when executed causes a computing system to control operations comprising:
    detecting a raw signal from a user via a motion sensor;
    determining a snoring signal from the raw signal based on an adaptive frequency threshold; and
    providing feedback to the user based on the snoring signal,
    wherein:
       the feedback comprises visual instruction to the user regarding sleeping position provided prior to determining the snoring signal.

11. An electronic device comprising:
    a motion sensor configured to detect a raw signal from a user;
    a processor configured to determine a snoring signal from the raw signal based on an adaptive frequency threshold; and
    an output device configured to provide feedback to the user based on the snoring signal,
    wherein:
       the feedback comprises visual instruction to the user regarding sleeping position provided prior to determining the snoring signal.

12. The electronic device of claim 11, wherein the output device is one or more of a vibration module, a speaker, and a visual display.

13. The electronic device of claim 11, wherein the motion sensor is one of an accelerometer and a gyrometer.

14. The electronic device of claim 11, wherein the processor is configured to pre-process the raw signal with one of time-domain processing and time-frequency processing.

15. The electronic device of claim 14, wherein the time-frequency processing comprises wavelets coefficient reconstruction.

16. The electronic device of claim 11, wherein, if there are multiple channels for monitoring the raw signal, the processor is configured to select one of the multiple channels for monitoring the raw signal.

17. The electronic device of claim 12, wherein the electronic device is configured to track a body position of the user.

18. The non-transitory machine-readable medium storing machine executable instructions that when executed causes a computing system to control operations of claim 10, comprising pre-processing the raw signal with one of time-domain processing and time-frequency processing, wherein the time-frequency processing comprises wavelets coefficient reconstruction.

19. The non-transitory machine-readable medium storing machine executable instructions that when executed causes a computing system to control operations of claim 10, comprising tracking a body position of the user.

20. The electronic device of claim 11, wherein the processor is configured to track a body position of the user.

* * * * *